United States Patent [19]

Berges

[11] 4,067,880

[45] Jan. 10, 1978

[54] INTERMEDIATES FOR PREPARING 7-ACYL-3-(SULFOALKYL SUBSTITUTED OXADIAZOLYLTHIOMETHYL)CEPHALOSPORINS

[75] Inventor: David A. Berges, Wayne, Pa.

[73] Assignee: SmithKline Corporation, Philadelphia, Pa.

[21] Appl. No.: 790,716

[22] Filed: Apr. 25, 1977

Related U.S. Application Data

[62] Division of Ser. No. 666,095, March 11, 1976, Pat. No. 4,041,162.

[51] Int. Cl.$^2$ .......................................... C07D 271/10
[52] U.S. Cl. ............................ 260/307 A; 260/307 G
[58] Field of Search ........................ 260/307 G, 307 A

[56] References Cited

U.S. PATENT DOCUMENTS 3,202,673   8/1965   Metivier et al. ..................... 260/307

Primary Examiner—Raymond V. Rush
Attorney, Agent, or Firm—Janice E. Williams; William H. Edgerton; Alan D. Lourie

[57] ABSTRACT

The compounds of this invention are cephalosporins having various acyl substituents at the 7-position and a sulfoalkyl substituted oxadiazolylthiomethyl group at the 3-position of the cephem nucleus and intermediates for the preparation thereof. The 7-acylated compounds have antibacterial activity.

2 Claims, No Drawings

INTERMEDIATES FOR PREPARING 7-ACYL-3-(SULFOALKYL SUBSTITUTED OXADIAZOLYLTHIOMETHYL)CEPHALOSPORINS

This is a division of application Ser. No. 666,095 filed Mar. 11, 1976, now U.S. Pat. No. 4,041,162.

This invention relates to a new series of cephalosporin compounds which have antibacterial activity when administered parenterally and to intermediates for the preparation thereof. In particular, the structures of the biologically active cephalosporin compounds of this invention are characterized by having a novelly substituted oxadiazolythiomethyl group at the 3-position of the cephem nucleus. Also, this invention extends to methods and compositions for treating certain bacterial infections using these new compounds as well as to certain chemical intermediates and methods for preparing the compounds described hereafter.

The compounds of this invention are represented by the following structural formula:

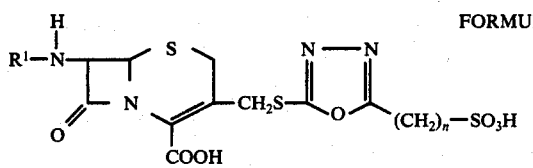

in which:
R$^1$ is an acyl group selected from the group consisting of:

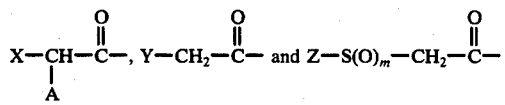

where:
X is thienyl, dihydrophenyl, phenyl or phenyl mono-substituted with hydroxy, hydroxymethyl, formamido, ureido or carboxymethylamino;
A is NH$_2$, OH, COOH or SO$_3$H; or formyloxy when X is phenyl;
Y is cyano, aminomethylphenyl, sydnone, pyridone, thienyl or tetrazolyl;
Z is methyl, trifluoromethyl, trifluoroethyl, pyridyl or cyanomethyl;
$m$ is 0 to 2; and
$n$ is 1 to 5, or a non-toxic pharmaceutically acceptable salt thereof.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such esters are included within the scope of this invention.

Preferred compounds of this invention are represented by Formula I where $n$ is one.

Advantageous compounds of this invention are represented by Formula I where $n$ is one and R$^1$ is

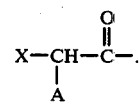

Most advantageous are the compounds represented by Formula I where $n$ is one, R$^1$ is

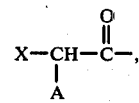

X is phenyl or hydroxyphenyl and A is NH$_2$ or OH.

Examples of the most preferred 7-acyl substituents (R$^1$NH—) of the compound of Formula I are listed below:

α-hydroxyphenylacetamido
α-aminophenylacetamido
α-amino-4-hydroxyphenylacetamido
trifluoromethylthioacetamido
methylthioacetamido
2,2,2-trifluoroethylsulfinylacetamido
cyanoacetamido
α-carboxythienylacetamido
α-carboxyphenylacetamido
α-sulfophenylacetamido
methylsulfonylacetamido
cyanomethylthioacetamido
α-amino-4-carboxymethylaminophenylacetamido
2-aminomethylphenylacetamido
3-sydnoneacetamido
1-tetrazolylacetamido
2-thienylacetamido
2-pyridoneacetamido
4-pyridoneacetamido
4-pyridylthioacetamido.

Particularly preferred is the compound 7-D-mandelamido-3-(5-sulfomethyl-1,3,4-oxadiazol-2-ylthiomethyl)-3-cephem-4-carboxylic acid.

Cephalosporin derivatives having 7-acyl substituents as defined above are well documented in the prior art. Substitution by variously substituted S-heterocyclicthiomethyl groups (—CH$_2$SHet) at the 3-position of the cephem nucleus, including carboxylic acid substituted heterocycles, is also known. However, no references to cephalosporin compounds containing the 3-(sulfoalkyl substituted oxadiazolyl)thiomethyl moiety disclosed herein are believed to be known to the art.

The compounds of Formula I are preferably prepared by acylating 7-aminocephalosporanic acid with an appropriately protected acylating agent and then displacing the 3-acetoxy group with the desired substituted oxadiazole thiol with subsequent removal of the protective group(s). The sulfoalkyloxadiazole thiols of the formula:

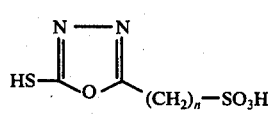

FORMULA II in which $n$ is 1 to 5,
are also objects of this invention, being important intermediates for producing pharmaceutical end products as described herein.

The carboxylic acid group of the acylating agent is activated by any of the standard methods such as conversion to the mixed anhydride, acid chloride, acid imidazolide or activated ester. In addition, a reagent such as dicyclohexylcarbodiimide can be used provided that the carboxyl group on the cephem nucleus is protected with an easily removable protecting group such as a benzhydryl, t-butyl, trichloroethyl, benzyl, benzyloxymethyl, p-methoxybenzyl or p-nitrobenzyl ester. When A is $NH_2$, the α-amino group of the acylating agent is, preferably, protected prior to acylation with an easily removable protective group known in the art such as t-butoxycarbonyl, trichloroethoxycarbonyl, benzyloxycarbonyl, the methyl acetoacetate adduct or similar groups commonly used in the synthesis of peptides.

Alternatively, the compounds of Formula I are prepared by acylation, as described above, of an appropriate 7-amino-3-(substituted oxadiazolylthiomethyl)cephalosporin nucleus of Formula III:

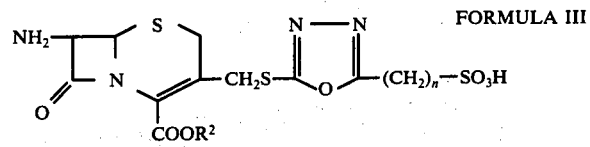

FORMULA III in which:
n is 1 to 5; and
$R^2$ is hydrogen or a protecting ester group,
with an appropriate acylating agent followed by removal of the protective groups when present. The compounds represented by Formula III are also considered as objects of this invention.

The protective groups can be removed according to methods well known to the art, such as with trifluoroacetic acid when t-butyl or t-butoxycarbonyl protective groups are used. The resulting salt is converted to the zwitterionic product or to the free acid by means of a basic ion exchange resin such as polystyrene-amine ion exchange resin (Amberlite IR-45) or else by basification of an aqueous solution of the salt.

The acylating agents used as starting materials are either known or prepared by known methods.

The 7-amino-3-(substituted oxadiazolythiomethyl)-cephalosporin starting materials of Formula III are prepared via reaction of 7-formamidocephalosporanic acid, prepared by reaction of 7-amino-cephalosporanic acid with formic acid and acetic anhydride, and a substituted oxadiazole thiol of Formula II followed by treatment with acid such as hydrochloric acid to remove the formyl group.

The sulfoalkyl substituted oxadiazole thiols are prepared by cyclization of the corresponding 2-(sulfoalkylcarbonyl)hydrazinecarbodithioic acids, preferably as the potassium or sodium salts, such as 2-(sulfoacetyl)hydrazinecarbodithioic acid dipotassium salt. The 2-(sulfoalkylcarbonyl)hydrazinecarbodithioic acids are prepared by conversion of a chloroalkanoic acid ester, such as ethyl chloroacetate, to a sulfoalkanoic acid ester which is subsequently treated with hydrazine to give a sulfoalkanoic acid hydrazide which upon treatment with carbon disulfide and base gives the desired 2-(sulfoalkylcarbonyl)hydrazinecarbodithioic acid.

Certain compounds of this invention are capable of forming salts with, for example, the alkali metals such as sodium or potassium, the alkaline earth metals such as calcium or with the ammonium cation. When A is $NH_2$, the compounds can exist as the zwitterion or as either an acid or base salt. These salts are prepared by standard methods using a wide variety of non-toxic pharmaceutically acceptable acids and bases known in the art and are also considered as objects of this invention.

It will be recognized that due to the asymmetric α-carbon atom in the 7-acetamido group of Formula I when $R^1$ is

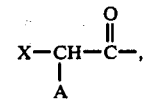

optical isomers will exist. Racemic or resolved products are obtained depending upon whether a racemic or resolved sidechain acid is used as an acylating agent. The resolved sidechain acids are readily obtained from the racemic compounds by resolution according to well known methods, including fractional crystallization of a salt formed with an optically active acid or base. All of the isomers, including separated isomers and mixtures thereof, are included within the scope of this invention.

The compounds of Formula I have exceptional antibacterial activity against both Gram-positive and Gram-negative organisms. Minimum inhibitory concentrations (MIC's) range from 0.2 to >200 μg./ml. in in vitro testing. Test results for the compound 7-D-mandelamido-3-(5-sulfomethyl-1,3,4-oxadiazol-2-ylthiomethyl)-3-cephem-4-carboxylic acid are given below:

| Bacteria | MIC (μg./ml.) |
|---|---|
| S. aureus HH 127 | 3.1 |
| S. aureus SK 23390 | 1.6 |
| S. villaluz SK 70390 | 200 |
| Strep. faecalis HH 34358 | 50 |
| E. coli SK 12140 | 1.6 |
| E. coli HH 33779 | 3.1 |
| Kleb. pneumo. SK 4200 | 1.6 |
| Kleb. pneumo. SK 1200 | 0.8 |
| Salmonella ATCC 12176 | 1.6 |
| Shigella HH 117 | 0.8 |
| Pseudo. aerug. HH 63 | >200 |
| Serratia marc. ATCC 13880 | 100 |
| Proteus morgani 179 | 25 |
| Entero aergo. ATCC 13048 | 3.1 |
| Entero. cloacae HH 31254 | 1.6 |

In the in vivo mouse protection test, 7-D-mandelamido-3-(5-sulfomethyl-1,3,4-oxadiazol-2-ylthiomethyl)-3-cephem-4-carboxylic acid exhibited $ED_{50}$'s of 1.56 mg./kg. against E. coli 12140 and 1.56 mg./kg. against Kleb. pneumo. 4200 upon subcutaneous injection.

Pharmaceutical compositions having antibacterial activity which comprise a pharmaceutical carrier containing an active but non-toxic quantity of a compound of Formula I as well as methods of combatting bacterial infections by administering such a composition to an infected host in a non-toxic amount sufficient to combat such infections are also objects of this invention. Administration is preferably by parenteral injection such as subcutaneously, intramuscularly or intravenously of suitably prepared sterile solutions or suspensions containing an effective, non-toxic amount of the new cephalosporin compound.

The compounds of Formula I are formulated and administered in the same manner as other cephalosporins. The dosage regimen comprises administration, preferably by injection, of an active but non-toxic quantity of a compound of Formula I selected from the dosage unit range of from 100 to 1000 mg. with the total daily dosage regimen being from 400 mg. to 6 g. The precise dosages are dependent upon the age and weight of the subject and on the infection being treated and can be determined by those skilled in the art based on the data disclosed herein compared with that available to the art attained with known cephalosporins.

The following examples illustrate the invention but are not to be construed as limiting the scope thereof. Temperatures are in degrees Centigrade (° C.) unless otherwise stated.

EXAMPLE 1

7-D-Mandelamido-3-(5-sulfomethyl-1,3,4-oxadiazol-2-ylthiomethyl)-3-cephem-4-carboxylic acid To a solution of 237 g (1.5 mol) of potassium sulfite in 150 ml of water was added 183 g (1.5 mol) of ethyl chloroacetate. The reaction mixture was refluxed for 4 hours then cooled and the solid was collected by filtration. Recrystallization from 70% ethanol gave the potassium salt of ethyl sulfoacetate.

A mixture of 148.7 g (0.72 mol) of the potassium salt of ethyl sulfoacetate and 32 g (1.0 mol) of hydrazine in 600 ml of water was refluxed for 12 hours. The solution was evaporated and the residual syrup was dissolved in 200 ml of water. The aqueous solution was filtered, diluted with methanol to turbidity and then cooled. The solid was collected by filtration and dried in vacuo to give sulfoacetyl hydrazide potassium salt (69%).

$C_2H_5N_2O_4S \cdot K$ —Calculated: 12.50%,C; 2.62%,H; 14.57%,N. Found: 12.66%,C; 2.75%,H; 14.71%,N.

To 91.9 g (0.478 mol) of sulfoacetyl hydrazide potassium salt was added a solution of 31.0 g (0.478 mol) of potassium hydroxide in 400 ml of water containing 225 ml of ethanol. The mixture was cooled to 5°–10° and 34.5 ml (0.574 mol) of carbon disulfide was added dropwise over a 10 minute interval. The mixture was stirred in the cold for 20 minutes then at ambient temperature for 12 hours. Ethanol (150 ml) was added and the mixture was cooled in ice. The precipitate was collected by filtration, washed with ethanol and air dried to give 2-(sulfoacetyl)hydrazinecarbodithioic acid dipotassium salt (81%).

$C_3H_4N_2O_4S_3 \cdot 2K$ —Calculated: 11.76%,C; 1.32%,H; 9.14%,N. Found: 11.59%,C; 1.67%,H; 9.18%,H.

A solution of 50.0 g (0.163 mol) of 2-(sulfoacetyl)hydrazinecarbodithioic acid dipotassium salt in 800 ml of 1:1 ethanol-water was refluxed for 12 hours. The mixture was evaporated to dryness and the residue was recrystallized from water to give 2-sulfomethyl-1,3,4-oxadiazole-5-thiol potassium salt, m.p. 276°–278° (dec.).

$C_3H_3N_2O_4S_2 \cdot K$ —Calculated: 15.38%,C; 1.29%,H; 11.96%,N. Found: 15.19%,C; 1.30%,H; 12.04%,N.

A solution of 2-sulfomethyl-1,3,4-oxadiazole-5-thiol potassium salt in water is passed through an Amberlite IR-120OH ion exchange resin colum to give, after lyophilization, 2-sulfomethyl-1,3,4-oxadiazole-5-thiol.

A mixture of 2.34 g (0.01 mol) of 2-sulfomethyl-1,3,4-oxadiazole-5-thiol potassium salt, 0.84 g (0.01 mol) of sodium bicarbonate and 2.85 g (0.0067 mol) of 7-D-mandelamidocephalosporanic acid sodium salt in 50 ml of water was stirred at 65°–68° for 5 hours. The reaction mixture was treated with 58.4 g of sodium chloride and additional water to give a nearly saturated solution and filtered. The filtrate was passed through a XAD-7 resin column with water as the eluant. The product-containing fraction was lyophilized and the lyophilized material was reprecipitated from methanol-water. The product was collected by filtration, washed with ether, taken up in water and lyophilized to give 7-D-mandelamido-3-(5-sulfomethyl-1,3,4-oxadiazol-2-ylthiomethyl)-3-cephem-4-carboxylic acid disodium salt.

$C_{19}H_{16}N_4O_9S_3 \cdot 2$ Na $\cdot 2.5$ $H_2O$ —Calculated: 36.13%,C; 3.35%,H; 8.87%,N. Found: 36.53%,C; 3.54%,H; 7.75%,N.

An aqueous solution of 7-D-mandelamido-3-(5-sulfomethyl-1,3,4-oxadiazol-2-ylthiomethyl)-3-cephem-4-carboxylic acid disodium salt is passed through a column of Amberlite IR-12OH ion exchange resin to give the title compound.

EXAMPLE 2

7-(D-α-Aminophenylacetamido)-3-(5-sulfomethyl-1,3,4-oxadiazol-2-ylthiomethyl)-3-cephem-4-carboxylic acid A solution of 7.58 g (0.015 mol) of 7-(D-α-t-butoxycarbonylaminophenylacetamido)cephalosporanic acid, 1.96 g (0.01 mol) of 2-sulfomethyl-1,3,4-oxadiazole-5-thiol and 2.94 g (0.035 mol) of sodium bicarbonate in 125 ml of water is stirred at 60° for 5 hours while maintaining the pH at 7.0–7.2 by addition of sodium bicarbonate. The mixture is cooled and extracted with ethyl acetate. The aqueous phase is acidified to pH 2.5 with 3N hydrochloric acid and the acidic solution is extracted again with ethyl acetate. The aqueous phase is brought to pH 7.1 by addition of 5% sodium carbonate solution, then passed through a XAD-4 ion exchange resin column and eluted with water and methanol to give 7-(D-α-t-butoxycarbonylaminophenylacetamido)-3-(5-sulfomethyl-1,3,4-oxadiazol-2-ylthiomethyl)-3-cephem-4-carboxylic acid disodium salt.

7-(D-α-t-Butoxycarbonylaminophenylacetamido)-3-(5-sulfomethyl-1,3,4-oxadiazol-2-ylthiomethyl)-3-cephem-4-carboxylic acid disodium salt is stirred at 25° with 25 ml of trifluoroacetic acid and 25 ml of 1,3-dimethoxybenzene for 2.25 hours. The mixture is evaporated to dryness, ether is added to the residue and the precipitate is collected, washed with ether, stirred in acetonitrile for 2 hours and dried in vacuo to give the title compound as the trifluoroacetic acid salt.

An aqueous solution of the trifluoroacetic acid salt is brought to pH 5.0 by addition of dilute aqueous sodium hydroxide. After lyophilization, the lyophilized material is dissolved in methanol and ether is added to precipitate 7-(D-α-aminophenylacetamido)-3-(5-sulfomethyl-1,3,4-oxadiazol-2-ylthiomethyl)-3-cephem-4-carboxylic acid sodium salt. The sodium salt is dissolved in water and the aqueous solution is passed through an Amberlite IR-120H ion exchange resin column. Lyophilization of the eluted material gives the title compound.

EXAMPLE 3

Reaction of the N-t-butoxycarbonyl derivative of the following cephalosporanic acids:

7-(α-amino-4-hydroxyphenylacetamido)cephalosporanic acid 7-(α-amino-4-formamidophenylacetamido)cephalosporanic acid 7-(α-amino-3-formamidophenylacetamido)cephalosporanic acid 7-(α-amino-4-ureidophenylacetamido)cephalosporanic acid 7-(α-amino-3-ureidophenylacetamido)cephalosporanic acid
7-(α-amino-4-hydroxymethylphenylacetamido)cephalosporanic acid
7-(α-amino-1,4-cyclohexadienylacetamido)cephalosporanic acid
7-(α-amino-4-carboxymethylaminophenylacetamido)cephalosporanic acid with 2-sulfomethyl-1,3,4-oxadiazole-5-thiol and sodium bicarbonate as described in the procedure of Example 2 followed by removal of the protective group and conversion of the trifluoroacetic acid salts to the free acids as described therein gives the following compounds of this invention:

7-(α-amino-4-hydroxyphenylacetamido)-3-(5-sulfomethyl-1,3,4-oxadiazol-2-ylthiomethyl)-3-cephem-4-carboxylic acid
7-(α-amino-4-formamidophenylacetamido)-3-(5-sulfomethyl-1,3,4-oxadiazol-2-ylthiomethyl)-3-cephem-4-carboxylic acid
7-(α-amino-3-formamidophenylacetamido)-3-(5-sulfomethyl-1,3,4-oxadiazol-2-ylthiomethyl)-3-cephem-4-carboxylic acid
7-(α-amino-4-ureidophenylacetamido)-3-(5-sulfomethyl-1,3,4-oxadiazol-2-ylthiomethyl)-3-cephem-4-carboxylic acid
7-(α-amino-3-ureidophenylacetamido)-3-(5-sulfomethyl-1,3,4-oxadiazol-2-ylthiomethyl)-3-cephem-4-carboxylic acid
7-(α-amino-4-hydroxymethylphenylacetamido)-3-(5-sulfomethyl-1,3,4-oxadiazol-2-ylthiomethyl)-3-cephem-4-carboxylic acid
7-(α-amino-1,4-cyclohexadienylacetamido)-3-(5-sulfomethyl-1,3,4-oxadiazol-2-ylthiomethyl)-3-cephem-4-carboxylic acid
7-(α-amino-4-carboxymethylaminophenylacetamido)-3-(5-sulfomethyl-1,3,4-oxadiazol-2-ylthiomethyl)-3-cephem-4-carboxylic acid.

EXAMPLE 4

7-(4-Hydroxymandelamido)-3-(5-sulfomethyl-1,3,4-oxadiazol-2-ylthiomethyl)-3-cephem-4-carboxylic acid is prepared by reaction of 7-(4-hydroxymandelamido)cephalosporanic acid sodium salt and 2-sulfomethyl-1,3,4-oxadiazole-5-thiol followed by treatment of the product with Amberlite IR-120H ion exchange resin as described in the procedure of Example 1.

EXAMPLE 5

When the sodium salt of a cephalosporanic acid listed below:

7-(3-sydnoneacetamido)cephalosporanic acid
7-(2-thienylacetamido)cephalosporanic acid
7-(1-tetrazolylacetamido)cephalosporanic acid
7-(2-aminomethylphenylacetamido)cephalosporanic acid suitably protected as necessary, is reacted with 2-sulfomethyl-1,3,4-oxadiazole-5-thiol by the procedure described in Example 1 and the product is deblocked when necessary and converted to the free acid as described therein, the following compounds of this invention are obtained, respectively:

7-(3-sydnoneacetamido)-3-(5-sulfomethyl-1,3,4-oxadiazol-2-ylthiomethyl)-3-cephem-4-carboxylic acid
7-(2-thienylacetamido)-3-(5-sulfomethyl-1,3,4-oxadiazol-2-ylthiomethyl)-3-cephem-4-carboxylic acid
7-(1-tetrazolylacetamido)-3-(5-sulfomethyl-1,3,4-oxadiazol-2-ylthiomethyl)-3-cephem-4-carboxylic acid
7-(2-aminomethylphenylacetamido)-3-(5-sulfomethyl-1,3,4-oxadiazol-2-ylthiomethyl)-3-cephem-4-carboxylic acid.

EXAMPLE 6

7-Trifluoromethylthioacetamido-3-(5-sulfomethyl-1,3,4-oxadiazol-2-ylthiomethyl)-3-cephem-4-carboxylic acid A solution of 1.96 g (0.01 mol) of 2-sulfomethyl-1,3,4-oxadiazole-5-thiol, 4.36 g (0.01 mol) of 7-trifluoromethylthioacetamidocephalosporanic acid sodium salt and 1.68 g (0.02 mol) of sodium bicarbonate in 50 ml of water is heated at 70° for 5.5 hours while maintaining the pH at 7.5 with 5% aqueous sodium bicarbonate. The reaction mixture is diluted with 50 ml of water and extracted twice with ethyl acetate. The aqueous phase is acidified to pH 2 and extracted three times with ethyl acetate. The aqueous layer is brought to pH 7.4 by addition of 5% aqueous sodium bicarbonate and the solution is passed through a XAD-4 resin column while eluting with water followed by methanol. The product-containing fractions are evaporated to dryness to give 7-trifluoromethylthioacetamido-3-(5-sulfomethyl-1,3,4-oxadiazol-2-ylthiomethyl)-3-cephem-4-carboxylic acid disodium salt.

7-Trifluoromethylthioacetamido-3-(5-sulfomethyl-1,3,4-oxadiazol-2-ylthiomethyl)-3-cephem-4-carboxylic acid disodium salt is converted to the title compound as described in Example 1.

EXAMPLE 7

Reaction of the sodium salt of a cephalosporanic acid listed below:

7-(2,2,2-trifluoroethylthioacetamido)cephalosporanic acid
7-methylthioacetamidocephalosporanic acid with 2-sulfomethyl-1,3,4-oxadiazole-5-thiol and sodium bicarbonate as described in the procedure of Example 6 gives, after conversion of the salts formed to the free acids, the following compounds of this invention as final products:

7-(2,2,2-trifluoroethylthioacetamido)-3-(5-sulfomethyl-1,3,4-oxadiazol-2-ylthiomethyl)-3-cephem-4-carboxylic acid
7-methylthioacetamido-3-(5-sulfomethyl-1,3,4-oxadiazol-2-ylthiomethyl)-3-cephem-4-carboxylic acid.

EXAMPLE 8

Reaction of a cephalosporanic acid listed below or its corresponding salt:

7-(α-hydroxy-2-thienylacetamido)cephalosporanic acid
7-(α-carboxy-2-thienylacetamido)cephalosporanic acid
7-(α-sulfophenylacetamido)cephalosporanic acid with 2-sulfomethyl-1,3,4-oxadiazole-5-thiol and sufficient sodium bicarbonate to convert the acidic functions to the corresponding sodium salts by procedures described hereinabove gives, after conversion of the product salts to the free acids, the following compounds of this invention:

7-(α-hydroxy-2-thienylacetamido)-3-(5-sulfomethyl-1,3,4-oxadiazol-2-ylthiomethyl)-3-cephem-4-carboxylic acid 7-(α-carboxy-2-thienylacetamido)-3-(5-sulfomethyl-1,3,4-oxadiazol-2-ylthiomethyl)-3-cephem-4-carboxylic acid 7-(α-sulfophenylacetamido)-3-(5-sulfomethyl-1,3,4-oxadiazol-2-ylthiomethyl)-3-cephem-4-carboxylic acid.

EXAMPLE 9

When an equivalent amount of a chloroalkanoic acid ester listed below:

3-chloropropionic acid ethyl ester
4-chlorobutyric acid ethyl ester
5-chlorovaleric acid ethyl ester
6-chlorohexanoic acid ethyl ester is substituted into the procedure of Example 1 in place of ethyl chloroacetate and the resulting sulfo acids are converted to the corresponding hydrazides which are subsequently treated with carbon disulfide to give sulfoalkylcarbonylhydrazinecarbodithioic acids which are then cyclized, all as described therein, the following 2-sulfoalkyl-1,3,4-oxadiazole-5-thiols are obtained as the corresponding potassium salts:

2-(2-sulfoethyl)-1,3,4-oxadiazole-5-thiol
2-(3-sulfopropyl)-1,3,4-oxadiazole-5-thiol
2-(4-sulfobutyl)-1,3,4-oxadiazole-5-thiol
2-(5-sulfopentyl)-1,3,4-oxadiazole-5-thiol.

The thiol potassium salts are converted to the free acids as described in Example 1.

Reaction of the potassium salt of a 2-sulfoalkyl-1,3,4-oxadiazole-5-thiol listed above with 7-D-mandelamidocephalosporanic acid sodium salt and one equivalent of sodium bicarbonate as described in Example 1, followed by conversion of the product salt formed to the free acid, gives the following compounds of this invention:

7-D-mandelamido-3-[5-(2-sulfoethyl)-1,3,4-oxadiazol-2-ylthiomethyl]-3-cephem-4-carboxylic acid
7-D-mandelamido-3-[5-(3-sulfopropyl)-1,3,4-oxadiazol-2-ylthiomethyl]-3-cephem-4-carboxylic acid
7-D-mandelamido-3-[5-(4-sulfobutyl)-1,3,4-oxadiazol-2-ylthiomethyl]-3-cephem-4-carboxylic acid
7-D-mandelamido-3-[5-(5-sulfopentyl)-1,3,4-oxadiazol-2-ylthiomethyl]-3-cephem-4-carboxylic acid.

EXAMPLE 10

7-Amino-3-(5-sulfomethyl-1,3,4-oxadiazol-2-ylthiomethyl)-3-cephem-4-carboxylic acid To a mixture of 97 g (2.1 mol) of formic acid, distilled from anhydrous copper sulfate, and 37.5 ml (0.4 mol) of acetic anhydride was added 25.0 g (0.1 mol) of 7-aminocephalosporanic acid. The mixture was stirred at ambient temperature for 0.5 hour, then evaporated to dryness. The residue was dissolved in ethyl acetate and the ethyl acetate solution was filtered and evaporated to dryness to give a residue which was recrystallized from ether-petroleum ether to give 7-formamidocephalosporanic acid.

A mixture of 1.0 g (3.3 mmol) of 7-formamidocephalosporanic acid, 0.51 g (2.6 mmol) of 2-sulfomethyl-1,3,4-oxadiazole-5-thiol and 0.71 g (8.5 mmol) of sodium bicarbonate in 15 ml of water is stirred at 65°–70° for 3 hours while maintaining the pH at 7.0. The mixture is cooled, acidified to pH 1.0 with hydrochloric acid and extracted with ethyl acetate. The extract is filtered and the filtrate is evaporated to dryness to give a residue which is dissolved in methanol. The methanol solution is filtered and ether is added. The precipitate is collected by filtration and dried to give the title compound.

EXAMPLE 11

7-(4-Pyridylthioacetamido)-3-(5-sulfomethyl-1,3,4-oxadiazol-2-ylthiomethyl)-3-cephem-4-carboxylic acid (4-Pyridylthio)acetyl chloride (0.53 g, 2.8 mmol) is dropwise added to a mixture of 1.0 g of 7-amino-3-(5-sulfomethyl-1,3,4-oxadiazol-2-ylthiomethyl)-3-cephem-4-carboxylic acid and 0.9 g (9.0 mmol) of triethylamine in 10 ml of dry dimethylformamide. The reaction mixture is stirred for 1.5 hour at −10°, then it is warmed to ambient temperature and stirred for 1 hour. The mixture is filtered and the filtrate is diluted with 200 ml of ether-petroleum ether. The precipitate is collected by filtration and dissolved in water. The aqueous solution is passed through an Amberlite IR-120H resin column and the product-containing fractions are lyophilized to give the title compound.

EXAMPLE 12

Acylation of 7-amino-3-(5-sulfomethyl-1,3,4-oxadiazol-2-ylthiomethyl)-3-cephem-4-caboxylic acid with an activated derivative of the following acids:

cyanoacetic acid
3-pyridylthioacetic acid
cyanomethylthioacetic acid
2,2,2-trifluoroethylsulfinylacetic acid
trifluoromethylsulfonylacetic acid
2-pyridone-N-acetic acid
4-pyridone-N-acetic acid as described in the procedure of Example 11 gives the following compounds of this invention:

7-cyanoacetamido-3-(5-sulfomethyl-1,3,4-oxadiazol-2-ylthiomethyl)-3-cephem-4-carboxylic acid
7-(3-pyridylthioacetamido)-3-(5-sulfomethyl-1,3,4-oxadiazol-2-ylthiomethyl)-3-cephem-4-carboxylic acid
7-cyanomethylthioacetamido-3-(5-sulfomethyl-1,3,4-oxadiazol-2-ylthiomethyl)-3-cephem-4-carboxylic acid
7-(2,2,2-trifluoroethylsulfinylacetamido)-3-(5-sulfomethyl-1,3,4-oxadiazol-2-ylthiomethyl)-3-cephem-4-carboxylic acid
7-trifluoromethylsulfonylacetamido-3-(5-sulfomethyl-1,3,4-oxadiazol-2-ylthiomethyl)-3-cephem-4-carboxylic acid
7-(2-pyridoneacetamido)-3-(5-sulfomethyl-1,3,4-oxadiazol-2-ylthiomethyl)-3-cephem-4-carboxylic acid 7-(4-pyridoneacetamido)-3-(5-sulfomethyl-1,3,4-oxadiazol-2-ylthiomethyl)-3-cephem-4-carboxylic acid.

EXAMPLE 13

7-(D-α-Formyloxyphenylacetamido)-3-(5-sulfomethyl-1,3,4-oxadiazol-2-ylthiomethyl)-3-cephem-4-carboxylic acid 7-Amino-3-(5-sulfomethyl-1,3,4-oxadiazol-2-ylthiomethyl)-3-cephem-4-carboxylic acid is reacted with the formate ester of D-mandeloyl chloride according to the procedure of Example 11 to give the title compound.

EXAMPLE 14

An injectable pharmaceutical composition is formed by adding sterile water or sterile solution (2 ml.) to 500 mg. of 7-D-mandelamido-3-(5-sulfomethyl-1,3,4-oxadiazol-2-ylthiomethyl)-3-cephem-4-carboxylic acid sodium salt.

Pharmaceutical compositions of the other antibacterial compounds disclosed above may be formulated in a similar manner.

What is claimed is:

1. A compound of the formula:

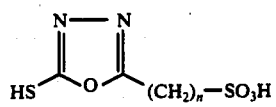

in which:
 $n$ is 1 to 5.

2. A compound according to claim 1, said compound being 2-sulfomethyl-1,3,4-oxadiazole-5-thiol.